United States Patent [19]

Eggersdorfer et al.

[11] Patent Number: 5,107,004
[45] Date of Patent: Apr. 21, 1992

[54] 2-NEOPENTYLANTHRAQUINONE, PROCESSES FOR ITS PREPARATION AND METHODS FOR ITS USE

[75] Inventors: Manfred Eggersdorfer, Frankenthal; Jochen Henkelmann, Mutterstadt; Walter Grosch, Edingen-Neckarhausen, all of Fed. Rep. of Germany

[73] Assignee: BASF Aktiengesellschaft, Ludwigshafen, Fed. Rep. of Germany

[21] Appl. No.: 362,403

[22] PCT Filed: Sept. 21, 1988

[86] PCT. No.: PCT/EP88/00854

§ 371 Date: May 23, 1989

§ 102(e) Date: May 23, 1989

[87] PCT Pub. No.: WO89/02886

PCT Pub. Date: Apr. 6, 1989

[30] Foreign Application Priority Data

Sep. 23, 1987 [DE] Fed. Rep. of Germany ....... 3732015

[51] Int. Cl.$^5$ ............................................. C07C 50/18
[52] U.S. Cl. ................................................... 552/268
[58] Field of Search ................. 552/268, 208; 423/588

[56] References Cited

U.S. PATENT DOCUMENTS

| | | | |
|---|---|---|---|
| 3,038,786 | 6/1962 | Hiratsaka et al. | 552/208 |
| 3,923,967 | 12/1975 | Kirchner et al. | 552/208 |
| 4,087,458 | 5/1978 | Emori et al. | 552/268 |
| 4,853,481 | 8/1989 | Henkelmann et al. | 562/460 |
| 4,895,984 | 1/1990 | Eggersdorfer et al. | 568/316 |

OTHER PUBLICATIONS

J. Chme. Soc. (C) 18 (1969), 2505-2506.

Primary Examiner—C. Warren Ivy
Assistant Examiner—Raymond Covington
Attorney, Agent, or Firm—Keil & Weinkauf

[57] ABSTRACT

The novel compound 2-neopentylanthraquinone which is prepared by Friedel-Crafts acylation of neopentylbenzene with phthalic anhydride and subsequent cyclization of the resulting 2-(4-neopentylbenzoyl)-benzoic acid in the presence of a strong, anhydrous acid, is a catalyst for the preparation of hydrogen peroxide.

2 Claims, No Drawings

2-NEOPENTYLANTHRAQUINONE, PROCESSES FOR ITS PREPARATION AND METHODS FOR ITS USE

The present invention relates to the novel compound 2-neopentylanthraquinone of the formula

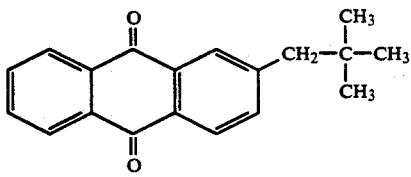

The present invention furthermore relates to the preparation of 2-neopentylanthraquinone by Friedel-Crafts acylation of neopentylglycol with phthalic anhydride and subsequent cyclization of the resulting 2-(4-neopentylbenzoyl)-benzoic acid in the presence of a strong, anhydrous acid.

The present invention also relates to the use of 2-neopentylanthraquinone as a catalyst in the preparation of hydrogen peroxide.

The industrially most important process for the preparation of hydrogen peroxide is the anthraquinone process. For this process, 2-alkylanthraquinones are required as catalysts.

In the process, which is carried out as a cyclic process, the dissolved 2-alkylanthraquinone is hydrogenated catalytically to the 2-alkylanthra hydroquinone, which, after removal of the hydrogenation catalyst, is oxidized back to the 2-alkylanthraquinone with oxygen. In this second step, hydrogen peroxide is formed and it is extracted from the reaction solution with water. The 2-alkylanthraquinone formed again is recycled into the recirculation. The process is described in more detail in, for example, Ullmann, Vol. 17, page 691 et seq., (4th Edition, Weinheim, New York, 1979).

The patent literature proposes various 2-alkylanthraquinones as catalysts in this process, for example 2-methyl-, 2-ethyl-, and 2-propylanthraquinone (U.S. Pat. No. 2,158,525), 2-isopropyl-, 2-sec-butyl- and 2-tert-butylanthraquinone (U.S. Pat. No. 2,935,381) and 2-amylanthraquinone (German Published Application DAS 1,112,051 and U.S. Pat. No. 3,041,143).

2-Amylanthraquinone is a mixture of roughly equal amounts of 2-tert-pentylanthraquinone and 2-(3-methylbut-2-yl)-anthraquinone. This mixture results from the first stage of the anthraquinone synthesis, ie. the Friedel-Crafts acylation of tert-pentylbenzene with phthalic anhydride, in which about half the tert-pentyl groups are isomerized to sec-pentyl groups.

2-Amylanthraquinone mixtures having a high content of tert-amylanthraquinone have proven particularly advantageous for the preparation of hydrogen peroxide (German Laid-Open Application DOS 2,013,299).

Although the isomerization of the tert-amyl group under the synthesis conditions can be partially suppressed, additional measures are required for this purpose (German Patent 2,720,294). Some of these additional measures require expensive technical apparatuses and give unsatisfactory yields.

High stability of the 2-alkylanthraquinone is important with regard to a long life of the 2-alkylanthraquinone/2-alkylanthrahydroquinone system. Furthermore, high solubility of the 2-alkylanthraquinone/2-alkylanthrahydroquinone system in the solvent systems used in the H2O2 preparation is advantageous for a good space-time yield of the hydrogen peroxide process.

However, the amylanthraquinone mixtures have the disadvantage that only the tert-amyl compound has good stability whereas 2-sec-isoamylanthraquinone undergoes oxidation under the reaction conditions of the H2O2 synthesis.

It is an object of the present invention to provide a catalyst for the hydrogen peroxide synthesis, which catalyst has high solubility in the quinone and hydroquinone forms in the reaction solution, has good stability under the conditions of the H2O2 synthesis and furthermore can be prepared in a simple and economical manner.

We have found that this object is achieved by the novel compound 2-neopentylanthraquinone of the formula

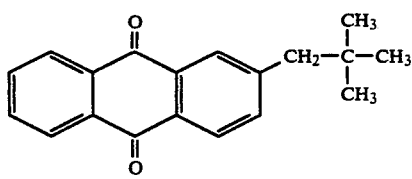

Furthermore, we have found a process for the preparation of 2-neopentylanthraquinone, wherein neopentylbenzene is acylated with phthalic anhydride by a Friedel-Crafts reaction to give 2-(4-neopentylbenzoyl)-benzoic acid and the latter is cyclized in the presence of a strong anhydrous acid to give 2-neopentylanthraquinone. We have also found that 2-neopentylanthraquinone is a catalyst for the preparation of hydrogen peroxide.

2-Neopentylanthraquinone is obtained from neopentylbenzene and phthalic anhydride in good yields without isomerization or degradation of the neopentyl group taking place.

In the synthesis of other 2-alkylanthraquinones, degradation of the alkyl group under the synthesis conditions oftens leads to the formation of undesirable by-products, for example anthraquinone, 2-methylanthraquinone and 2-isopropylanthraquinone, which present problems in the H2O2 synthesis and therefore have to be separated off in expensive purification steps.

Since no such byproducts are formed in the synthesis of 2-neopentylanthraquinone, this expensive purification can be dispensed with.

In the novel process, neopentylbenzene (1) is acylated in a first step with phthalic anhydride (2) under Friedel-Crafts conditions to give 2-(4-neopentylbenzoyl)-benzoic acid (3).

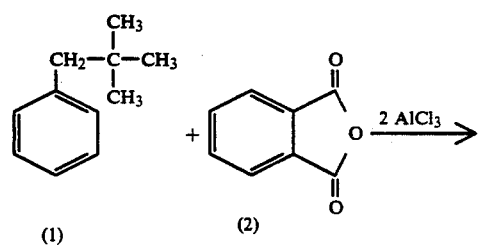

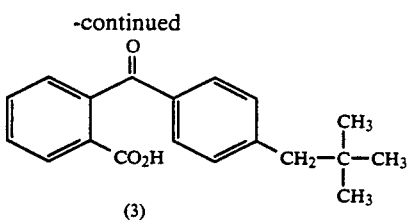

(3)

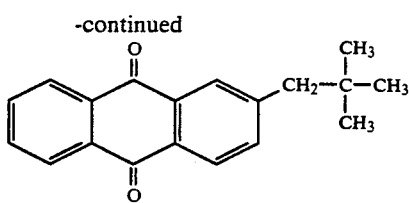

Neopentylbenzene is a known compound and is described in J. Chem. Soc. (C) 18 (1969), 2505-2506.

The conventional compounds, such as $FeCl_3$, $BF_3$, $ZnCl_2$ and $TiCl_4$, can be used as Friedel-Crafts catalysts for this reaction. Aluminum halides, preferably aluminum bromide and in particular aluminum chloride, are particularly suitable. Mixtures of these catalysts can also be used.

The amounts of catalyst usually used for Friedel-Crafts reactions can also be used in the novel process, 2 moles of catalyst per mole of phthalic anhydride advantageously being employed. However, it is also possible to use an excess of catalyst, for example from 2.1 to 3.5 moles of catalyst per mole of phthalic anhydride.

Advantageously stoichiometric amounts of neopentylbenzene and phthalic anhydride are used. It is however also possible to employ one of the two components in an excess amount relative to the other. For example, from 1 to 1.5 moles of neopentylbenzene can be used per mole of phthalic anhydride or vice versa.

The reaction is carried out in the absence or, advantageously, in the presence of a solvent, suitable solvents being, for example, chlorobenzene, dichlorobenzene, trichlorobenzene, 1,2-dichloroethane, carbon disulfide, nitromethane and nitrobenzene. The amount of solvent is variable and in general from 200 to 1,000 g of solvent can be used per mole of neopentylbenzene.

The reaction is advantageously carried out by reacting the starting materials at from $-20°$ to $100°$ C., preferably from $0°$ to $60°$ C., in particular from $10°$ to $40°$ C., under superatmospheric or reduced pressure, but preferably under atmospheric pressure.

Advantageously, the phthalic anhydride is initially taken together with the solvent, and the Friedel-Crafts catalyst and then the neopentylbenzene are added, although the converse sequence is also possible.

Working up of the reaction mixture and isolation of the product is generally carried out in a conventional manner by pouring the reaction mixture onto water and/or ice, separating off the aqueous phase and then isolating the 2-(4-neopentylbenzoyl)-benzoic acid from the organic phase.

The 2-(4-neopentylbenzoyl)-benzoic acid (3) is advantageously cyclized in the presence of a strong, anhydrous acid to give 2-neopentylanthraquinone (cf. equation).

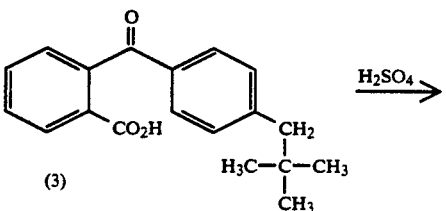

The cyclization of the 2-(4-neopentylbenzoyl)-benzoic acid is advantageously carried out in a conventional manner, for example by the methods described in Houben-Weyl, Vol. 7/3c, pages 35-39, advantageously with from 95 to 105% strength sulfuric acid (=5% strength oleum), preferably with 100% strength sulfuric acid.

Advantageously, the sulfuric acid is initially taken and the 2-(4-neopentylbenzoyl)-benzoic acid is added to it. The amount of sulfuric acid is in general from 0.5 to 10, preferably from 0.8 to 1.0, kg per kg of the 2-(4-neopentylbenzoyl)-benzoic acid. The reaction mixture is then stirred in general for from 1 to 10 hours at from 20 to 220° C., preferably, however, at from 60° to 90° C. The reaction can be carried out under atmospheric, superatmospheric or reduced pressure.

The reaction is terminated by pouring the reaction mixture into, for example, ice and/or water. The product can then be isolated from the reaction mixture by extraction with a suitable solvent. Examples of suitable solvents are aromatic hydrocarbons, such as benzene, toluene and xylene, and chlorohydrocarbons, such as chlorobenzene, dichloromethane, dichloroethane and trichloroethane.

The solution of the 2-neopentylanthraquinone is advantageously washed neutral with dilute sodium hydroxide solution and then with water. The solvent is removed and the product then isolated.

However, working up can also be effected in the absence of a solvent. In an advantageous procedure of this type, the reaction is terminated by pouring the reaction mixture into water and/or ice and the precipitated reaction product is filtered off. After the reaction product has been washed neutral, the 2-neopentylanthraquinone is isolated from it, preferably by distillation under reduced pressure. This procedure results in not only lower solvent consumption but also less environmental pollution due to solvent emissions.

2-Neopentylanthraquinone is very suitable as a catalyst for the preparation of hydrogen peroxide by the anthraquinone process (Ullmanns Enzyclopädie der Technischen Chemie, Vol. 17, page 691 et seq., 4th Edition, Weinheim, 1979). However, it can also advantageously be used as a catalyst in mixtures with other anthraquinones, such as 2-methylanthraquinone, 2-ethylanthraquinone, 2-propylanthraquinone, 2-isopropylanthraquinone, 2-secbutylanthraquinone, 2-tert-butylanthraquinone and 2-amylanthraquinone. The mixing ratio may vary within wide limits since this depends on the one hand on the type of 2-alkylanthraquinones admixed and on the other hand on the particular process conditions (temperature, solvent, etc.) in the relevant plants for the preparation of hydrogen peroxide.

EXAMPLE 74 g (0.5 mole) of phthalic anhydride were dissolved in 250 ml of o-dichlorobenzene. 128 g (1.05 moles) of $AlCl_3$ were added a little at a time at from 15° to 20° C.

74 g (0.5 mole) of neopentylbenzene were then added dropwise at 20° C. in the course of 3 hours. Stirring was then continued for 1 hour at 40° C.

After the end of the reaction, the reacted mixture was poured onto a mixture of 1 l of water with 300 g of ice and 30 ml of concentrated $H_2SO_4$. The organic phase was washed neutral with dilute sodium hydroxide solution. Thereafter, the neopentylbenzoylbenzoic acid was precipitated from the aqueous phase with sulfuric acid and was dried. 140.8 g (95%) of 2-(4-neopentylbenzoyl)-benzoic acid (mp. 154.2° C.) were obtained.

90 g (0.3 mole) of this 2-(4-neopentylbenzoyl)-benzoic acid were introduced into 900 g of 100 percent strength sulfuric acid at 60° C. and then stirred for 4 hours at 85° C. The reaction mixture was then poured into a mixture of 1,500 g of water and 500 g of ice, and the stirred mixture was cooled. The precipitated crystals of neopentylanthraquinone were filtered off, washed neutral with dilute sodium hydroxide solution and water, dried, and distilled at 240° C./0.5 mbar. 75.3 g (89%) of 2-neopentylanthraquinone (mp. 93.8° C.) were obtained.

We claim:

1. A process for the preparation of 2-neopentylanthraquinone, wherein neopentylbenzene is acylated with phthalic anhydride by a Friedel-Crafts reaction to give 2-(4-neopentylbenzoyl)-benzoic acid and the latter is cyclized in the presence of a strong anhydrous acid to give a composition consisting essentially of 2-neopentylanthraquinone without isomerization or degradation of the neopentyl group taking place.

2. A process as claimed in claim 1, wherein the cyclization is carried out with from 95 to 105% strength sulfuric acid at from 20° to 220° C.

* * * * *